United States Patent
Lint et al.

(10) Patent No.: US 9,449,503 B2
(45) Date of Patent: Sep. 20, 2016

(54) CIRCUIT BOARD FOR CONTROLLING WIRELESS DENTAL FOOT PEDAL

(71) Applicant: DENTSPLY INTERNATIONAL INC., York, PA (US)

(72) Inventors: Kevin Kenneth Lint, Seven Valleys, PA (US); Joseph Robert Reagan, Steelton, PA (US)

(73) Assignee: Dentsply International Inc., York, PA (US)

(*) Notice: Subject to any disclaimer, the term of this patent is extended or adjusted under 35 U.S.C. 154(b) by 0 days.

(21) Appl. No.: 14/042,813

(22) Filed: Oct. 1, 2013

(65) Prior Publication Data

US 2014/0038129 A1 Feb. 6, 2014

Related U.S. Application Data

(63) Continuation of application No. 13/084,814, filed on Apr. 12, 2011, now abandoned.

(60) Provisional application No. 61/323,129, filed on Apr. 12, 2010, provisional application No. 61/323,159, filed on Apr. 12, 2010, provisional application No. 61/323,120, filed on Apr. 12, 2010, provisional application No. 61/323,142, filed on Apr. 12, 2010.

(51) Int. Cl.
| | |
|---|---|
| *A61C 1/00* | (2006.01) |
| *G05G 1/46* | (2008.04) |
| *G08C 19/00* | (2006.01) |
| *A61B 17/00* | (2006.01) |

(52) U.S. Cl.
CPC .......... *G08C 19/00* (2013.01); *A61C 1/0015* (2013.01); *A61C 1/0023* (2013.01); *G05G 1/46* (2013.01); *A61B 2017/00225* (2013.01)

(58) Field of Classification Search
CPC ............. A61B 2017/00225; A61C 1/0015; A61C 1/0023; G05G 1/46; G08C 19/00
USPC ............ 340/12.22, 407.1; 433/101; 345/184; 68/12.01
See application file for complete search history.

(56) References Cited

U.S. PATENT DOCUMENTS

| | | | |
|---|---|---|---|
| 5,423,231 A | 6/1995 | Helfrich et al. | |
| 6,768,425 B2 * | 7/2004 | Flaherty et al. | 340/870.07 |
| 6,866,507 B2 * | 3/2005 | Beerstecher | 433/101 |
| 6,976,843 B2 | 12/2005 | Feine | |
| 7,012,203 B2 | 3/2006 | Hanson et al. | |
| 7,422,432 B2 | 9/2008 | Warner | |

(Continued)

FOREIGN PATENT DOCUMENTS

WO 2007092238 A2 8/2007

OTHER PUBLICATIONS

International Search Report, Application No. 2011/032049, Dated Sep. 29, 2011.

(Continued)

*Primary Examiner* — Fekadeselassie Girma
*Assistant Examiner* — Chico A Foxx
(74) *Attorney, Agent, or Firm* — McNees Wallace & Nurick LLC

(57) ABSTRACT

A system, method, and apparatus including a printed circuit board with electronic circuit components mounted thereon and configured for wireless communication between the various components and devices used in a wireless dental device.

15 Claims, 5 Drawing Sheets

(56) References Cited

U.S. PATENT DOCUMENTS

| | | |
|---|---|---|
| 7,439,463 B2 | 10/2008 | Brenner et al. |
| 2003/0163287 A1 | 8/2003 | Vock et al. |
| 2003/0169057 A1* | 9/2003 | Ishiguro et al. ............ 324/661 |
| 2003/0232305 A1 | 12/2003 | Warner |
| 2004/0115591 A1 | 6/2004 | Warner |
| 2005/0201549 A1* | 9/2005 | Dedieu et al. .......... 379/420.01 |
| 2006/0227030 A1* | 10/2006 | Clifford et al. ............... 341/176 |
| 2007/0031780 A1* | 2/2007 | Warner et al. ................ 433/101 |
| 2007/0031781 A1 | 2/2007 | Warner et al. |
| 2007/0166661 A1* | 7/2007 | Brenner et al. ............. 433/101 |
| 2007/0166662 A1* | 7/2007 | Lint et al. .................... 433/101 |
| 2007/0186594 A1* | 8/2007 | Kim et al. .................. 68/12.01 |
| 2007/0254261 A1 | 11/2007 | Rosenblood et al. |
| 2008/0166685 A1 | 7/2008 | Rosenblood et al. |
| 2009/0080348 A1* | 3/2009 | Hamel et al. ................ 370/310 |
| 2009/0225985 A1* | 9/2009 | Dolev et al. ................. 380/270 |
| 2009/0272221 A1 | 11/2009 | Long et al. |
| 2009/0284498 A1* | 11/2009 | Hayward ..................... 345/184 |
| 2010/0073150 A1* | 3/2010 | Olson et al. ............... 340/407.1 |
| 2010/0122565 A1* | 5/2010 | Miller et al. .................. 73/1.37 |
| 2011/0080349 A1* | 4/2011 | Holbein et al. .............. 345/173 |
| 2012/0062470 A1* | 3/2012 | Chang .......................... 345/173 |

OTHER PUBLICATIONS

International Written Opinion, Application No. PCT/US2011/032049, Dated Sep. 29, 2011.

* cited by examiner

CIRCUIT BOARD FOR CONTROLLING WIRELESS DENTAL FOOT PEDAL

This application claims priority to and the benefit of U.S. Provisional Patent Application No. 61/323,142 filed Apr. 12, 2010; U.S. Provisional Patent Application No. 61/323,129 filed Apr. 12, 2010; U.S. Provisional Patent Application No. 61/323,159 filed Apr. 12, 2010; and U.S. Provisional Patent Application No. 61/323,120 filed Apr. 12, 2010 all of which are hereby incorporated by reference in their entirety.

FIELD OF THE DISCLOSURE

The present disclosure is directed to a controller for dental instruments. More particularly, the disclosure relates to a circuit board mounted inside of a dental foot pedal housing having a wireless communications chip for controlling dental operatory instruments.

BACKGROUND OF THE DISCLOSURE

Dental and medical professionals use many instruments that are controlled by separate, discrete control devices. For example, surgical cutting instruments, ultrasonic dental scalars, endoscopic tools, irrigation and aspiration tools, dental drills, air polishers, other low speed hygiene handpieces, and dental prophylaxis units can be activated with foot control systems. The foot control system typically includes a foot pedal device that is placed on the floor within easy reach of the practitioner. The foot pedal is used to activate a dental/medical apparatus, which includes a base operating unit. The available foot pedals include both "hardwired" systems and wireless foot control systems. The base unit may be activated by depressing the foot pedal, which initiates communication with the base operating unit. The base operating unit is then in communication with the instrument, for example, a dental handpiece.

Such foot pedals need to be robust to withstand rough treatment that is encountered by foot-actuated devices, since pressure applied by the foot is normally greater than that which is applied by hand-operated devices. Also, the foot pedal is normally located on the floor where it may be accidentally kicked, upset, or otherwise exposed to moving or falling objects. Existing foot pedals are thus typically equipped with few electrical or electronic elements, such as spring actuated switches and position sensors, which transmit control signals to a remotely positioned controller by wired connections. The remotely positioned controller may house less sturdy electronic circuitry for controlling wireless communications between the foot pedal and the medical or dental instruments that are being remotely controlled by the foot pedal.

Therefore, what is needed is a wireless dental hygiene system that is modular, that includes reduced costs of certain portions, reduces or eliminates surfaces and/or regions where undesirable substances may be deposited, and improves capability for disinfection. What is also needed is an electronic circuit or circuit board for communication between the cordless dental hygiene system components, such as the foot pedal and the various hand pieces.

SUMMARY OF THE DISCLOSURE

One aspect of the disclosure includes a printed circuit board for a wireless foot pedal control system. The printed circuit board includes a substrate for mounting a plurality of electronic components. The electronic components include a programmable controller having a memory for storing software and data: a radio frequency (RF) transceiver which is arranged for wireless communications with at least one remote device; an accelerometer; a wake-up device for generating a wake-up signal to the programmable controller; and an antenna communicatively coupled with the RF transceiver. The electronic components are in electronic communication through printed circuit traces on the substrate, to control wireless communications between the foot pedal and one or more remote wireless devices.

Another aspect of the disclosure includes a wireless foot pedal controller for communication with at least one wireless dental instrument. The wireless foot pedal controller includes a housing, a power source and a printed circuit board positioned within the housing. The printed circuit board is connected to receive power from the power source, and includes an analog to digital converter. The printed circuit board also includes a substrate for mounting a plurality of electronic components. The electronic components include a programmable controller having a memory for storing software and data; a radio frequency transceiver which is arranged for wireless communications with at least one remote device; an accelerometer; a wake-up device for generating a wake-up signal to the programmable controller; and an antenna communicatively coupled with the RF transceiver. The electronic components are in electronic communication through printed circuit traces on the substrate, to control wireless communications between the foot pedal and one or more remote wireless devices.

BRIEF DESCRIPTION OF THE DRAWINGS

Wherever possible, the same reference numbers will be used throughout the drawings to represent the same parts.

DETAILED DESCRIPTION OF THE DISCLOSURE

The present disclosure now will be described more fully hereinafter with reference to the accompanying drawings, in which an exemplary embodiment of the disclosure is shown. This disclosure may, however, be embodied in many different forms and should not be construed as limited to the embodiments set forth herein.

Figure 1:
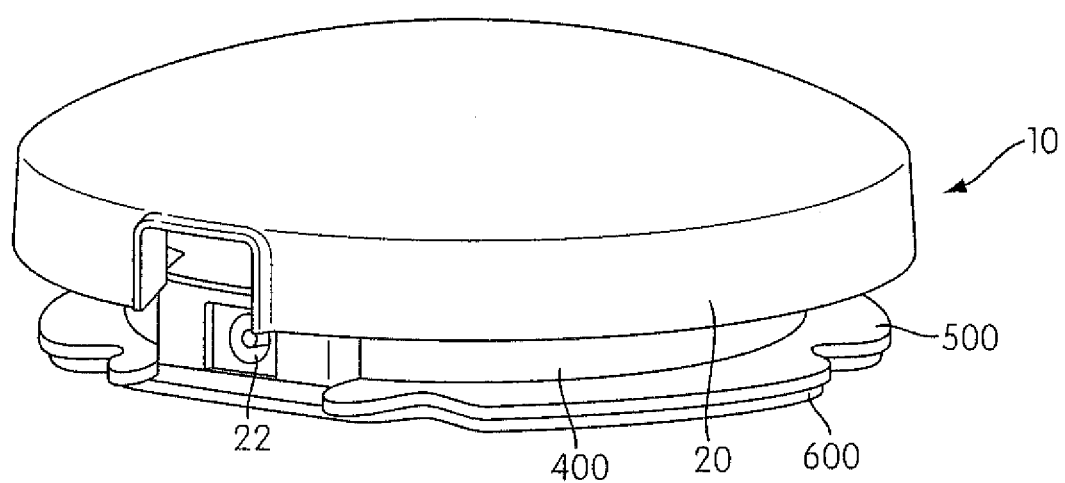
FIG. 1 is a perspective view of the foot pedal of the present invention.

FIG. 1 is a perspective view of a cordless foot pedal 10 of the present invention. A cover 20 hides the foot pedal internals from view, although a charge connector 22 is visible. Charge connector 22 accepts an electrical cord for recharging a battery positioned inside cover 20. Foot pedal 10 sits on a base having a rubber pad 600 which is spaced from cover 20. Base 600 supports lower housing 500 and upper housing 400.

Figure 2:
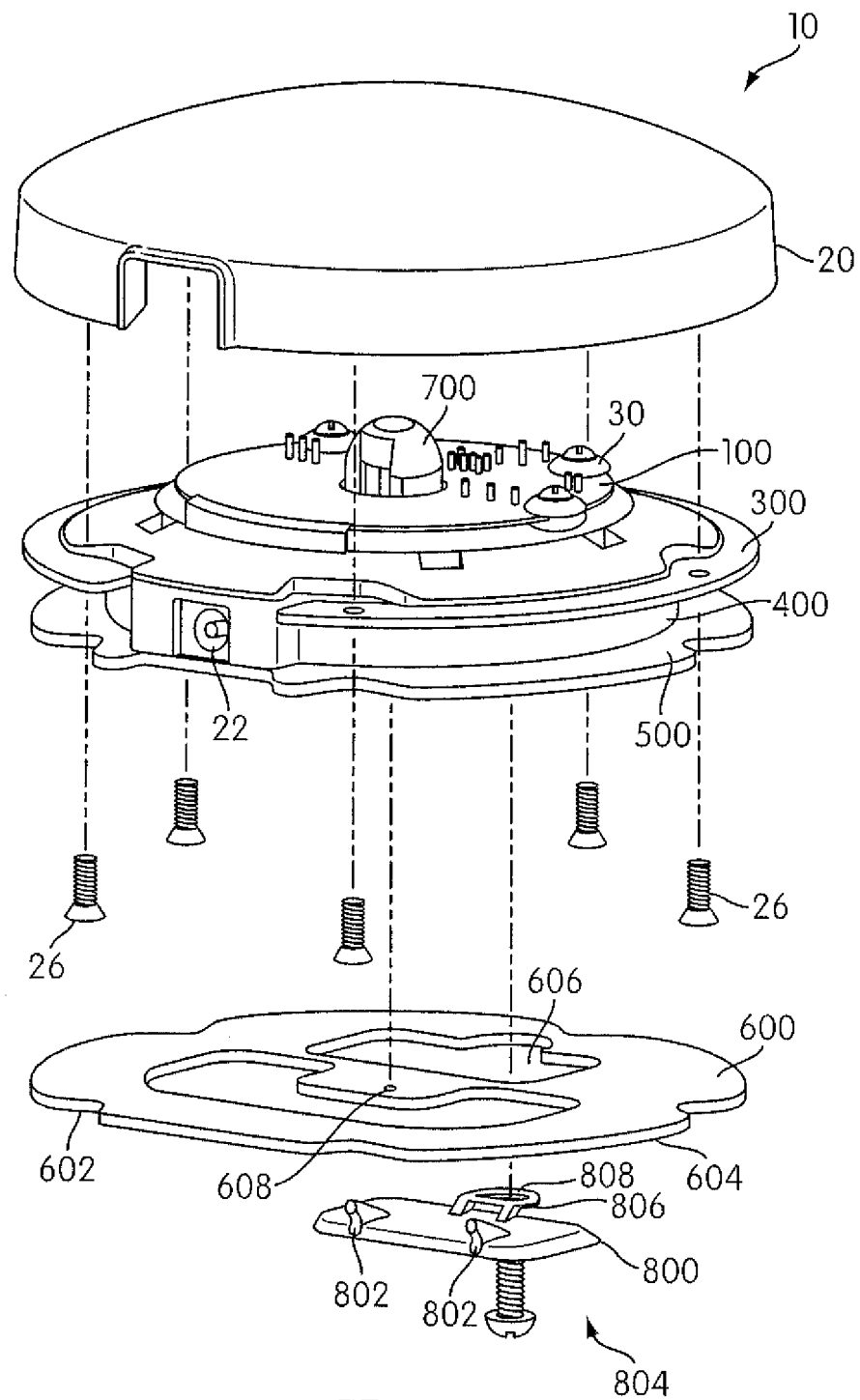
FIG. 2 is a partially exploded view of the foot pedal of FIG. 1.
Figure 3:
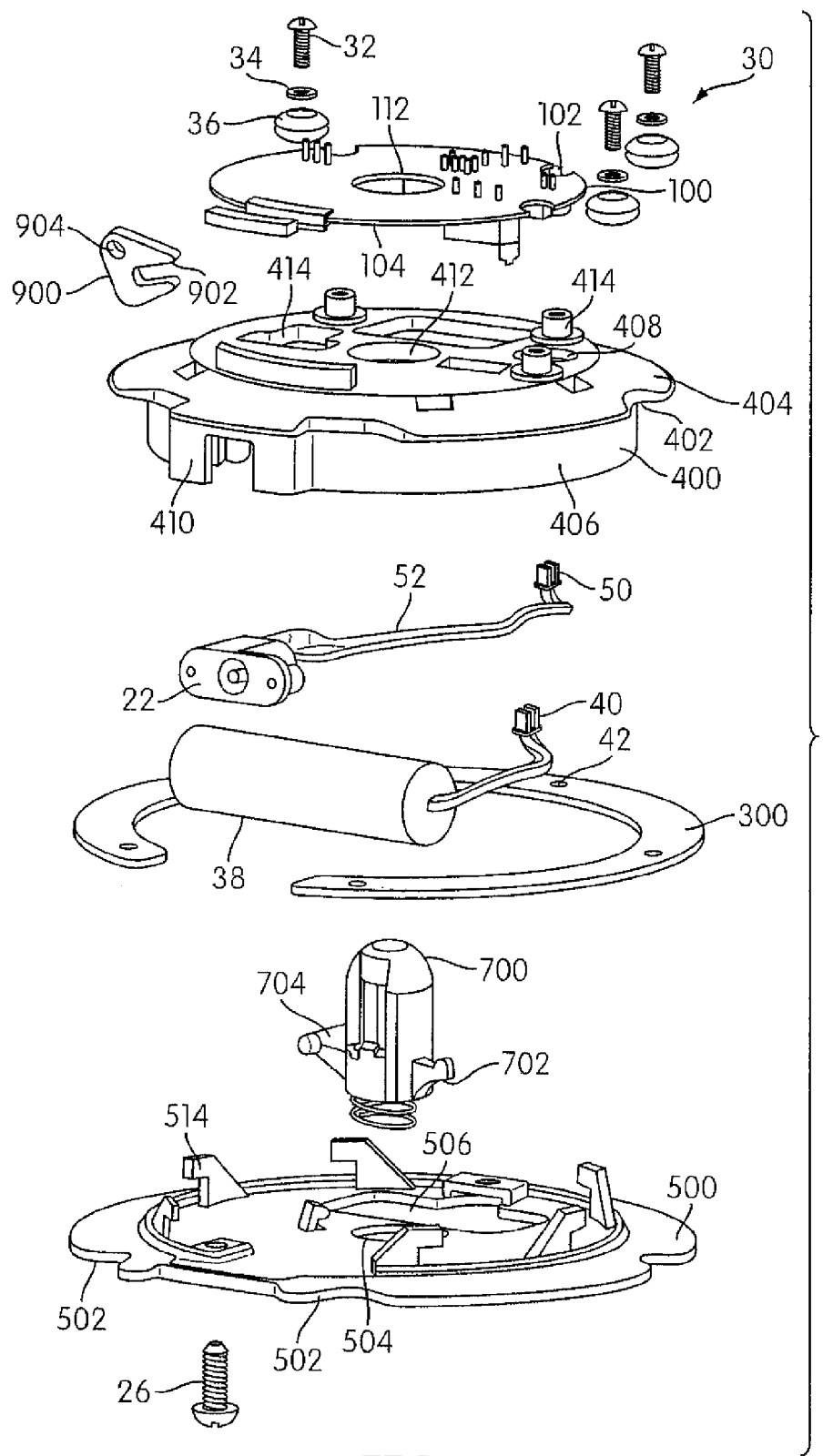
FIG. 3 is a fully exploded view of the printed circuit board assembly, the upper housing and lower housing of the present invention.

FIG. 2 is a partially exploded view of cordless foot pedal 10, displaying the internal arrangement within cover 20. Printed circuit board (PCB) assembly overlies upper housing 400, which is spaced from lower housing 500. Holding ring 300 is fastened to cover 20 by fastener 26, and upper surface 404 (FIG. 3) of upper housing 400 is captured between cover 20 and holding ring 300. Lower housing 500 is attached to upper housing 400 and restrained from rotation by anti-rotation fasteners 804, 26. PCB assembly 100 is attached to upper housing 400 by fastener assemblies 30. Charge connector 22 is visible on a wall of upper housing 400. Plunger housing assembly 700 extends through an aperture in PCB assembly 100. Screws 26 extend through scallops 502, 402 in lower housing 500 and upper housing 400 and through apertures 302 in holding ring 300. Screws 26 are captured in corresponding female threaded regions (not visible) that may be molded into cover 20. An anti-skid bottom 600 is adhesively or otherwise affixed to lower housing 500. Anti-skid bottom 600 includes scallops 602 that allow anti-skid bottom 600 to be assembled over screws 26 (FIG. 3). Lower housing 500 may be rotated within upper housing 400 and held in place in lower housing 500 by corresponding features, such as flanges, not visible in upper housing 400. Access cover 800 is also visible in FIG. 2. Access cover 800 slides into aperture 606 and into a mating feature in lower housing 500. Access cover 800 includes a pair of tabs 802 that extend onto one side of lower housing 500 while screw 804 slides through an aperture 808 in lock tab 806 and into a female threaded receiver (not visible) in lower housing 500, thereby locking access cover 800 in place. Alternatively, lock tab aperture 808 may be threaded to capture screw 804. Access cover 800 provides access to the interior of foot pedal 10 through aperture 606, and importantly to a bottom surface of PCB assembly 100 by simply removing screw 804 and sliding access cover 800 from lower housing 500, without the need to completely disassemble lower housing 500 from upper housing 400, in order to provide access to communication test pads on PCB assembly 100. Cordless foot pedal 10 is free to move along a floor, and cover 20, as will become clear, can move with respect to the remaining portions of the foot pedal 10.

FIG. 3 is a further exploded view of the upper housing 400, the lower housing 500 and portions of foot pedal 10 either attached to upper housing 400 and lower housing 500 or captured within upper housing 400 and lower housing 500.

Upper housing 400 is shown having an upper surface 404 and a vertical surface 406. A charge connector aperture 410 penetrates vertical surface 406 that receives charge connector 22. Upper surface 404 includes a central aperture 412, through with plunger assembly 700 extends. Upper surface 404 also includes a plurality of female thread housings 408. Upper surface further includes additional apertures 414, whose purpose will be readily apparent below.

Also shown in FIG. 3 is PCB assembly 100. PCB assembly 100 includes a plurality of scallops 102 and has an upper surface 104 and a lower surface 106. Upper surface 104 and lower surface 106 are shown in detail in FIGS. 5 and 6 and are further discussed below. PCB assembly 100 is assembled to upper housing 400 using a plurality of fastener assemblies 30. Each fastener assembly 30 comprises a screw 32, a washer 34 and grommet 36. Each grommet 36 is assembled along the edge of PCB assembly 100 at each scallop 102. Grommets 36 are then assembled over female thread housings 408, and washers 34 are assembled over grommets 36 and screws 32 secure fastener assemblies 30 to 408, thereby securing PCB assembly 100 to upper housing 400.

FIG. 3 also shows lower housing 500, plunger housing assembly 700, battery 38, charge connector 22 and holding ring 300. Plunger housing assembly sits on lower housing 500, extending through holding ring 300, upper housing central aperture 412 and PCB assembly center aperture 112. Plunger housing assembly 700 includes two arms. First arm is a plunger arm 702 while second arm is a potentiometer coupling area 704. Also depicted in FIG. 3 is a potentiometer adaptor lever 900. Lever 900 includes a slot 902 and an aperture 904. When assembled, potentiometer coupling arm 704, plunger arm 702 and lever 900 are positioned below printed circuit board assembly 100, even though a portion of plunger housing assembly 700 may protrude through central aperture 112. Slot 902 of potentiometer adaptor lever 900 fits over potentiometer coupling arm 704 of plunger housing assembly 700. Any movement of plunger housing assembly 700 will cause movement of potentiometer coupling arm 704 which will cause movement of potentiometer adaptor lever 900 as slot 902 moves with plunger arm 702.

Also depicted in FIG. 3 is battery 38 and charge connector 22. A first electrical connector 40 is attached to battery 38 via first wire 42. A second electrical connector 50 is also attached to charge connector 22 via a second wire 52. When assembled, fastener assemblies 30 attach PCB assembly 100 to female thread housings 408 in upper housing 400. Screws 26 attach holding ring 300 to cover 20, capturing upper housing 400 and holding ring 300. Lower housing 500 is assembled into upper housing 400 with scallops 502 over screws 26 and rotated. As shown in FIG. 3, rotation is counterclockwise. On rotation, notched flanges 514 positively engage cross-members (not visible) in upper housing 400 to lock lower housing 500 in position with respect to upper housing. Charge connector 22 is seated in charge connector aperture 410 by any convenient means. It may be held in, for example, with fasteners, or it may be held in place by a snap-fit. Battery 38 and wires 42 and 52 reside in the space between upper housing 400 and lower housing 500. Tabs may be included on the bottom of upper housing 400 for wire management for battery wires 42, 52.

Figure 4:
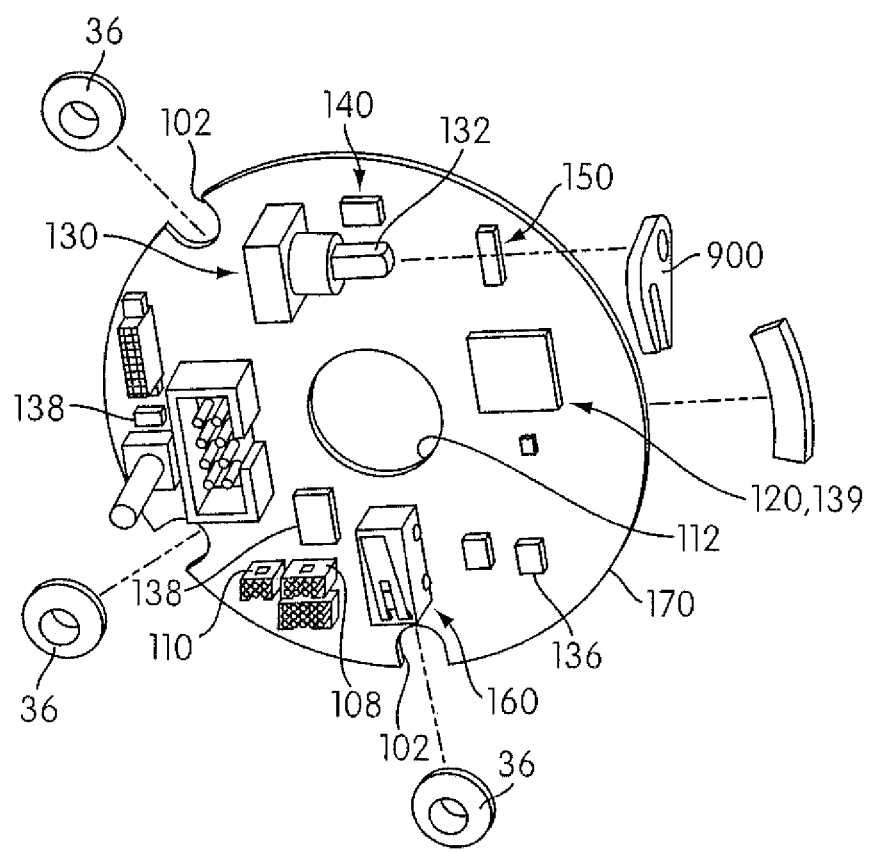
FIG. 4 is a top view of the upper surface of the printed circuit board assembly.
Figure 5:
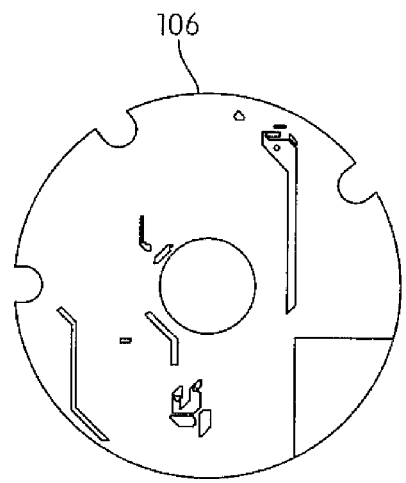
FIG. 5 is a plan view of the lower surface of the printed circuit board assembly.
Figure 6:
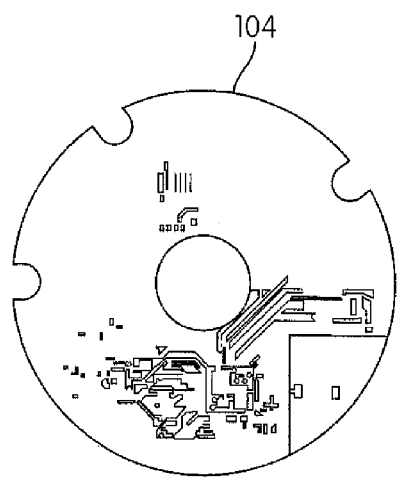
FIG. 6 shows a plan view of the top surface of the printed circuit board assembly.
Figure 7:
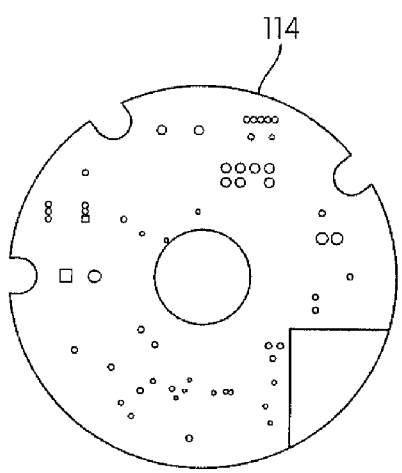
FIG. 7 shows a plan view of the ground plane of the printed circuit board assembly.
Figure 8:
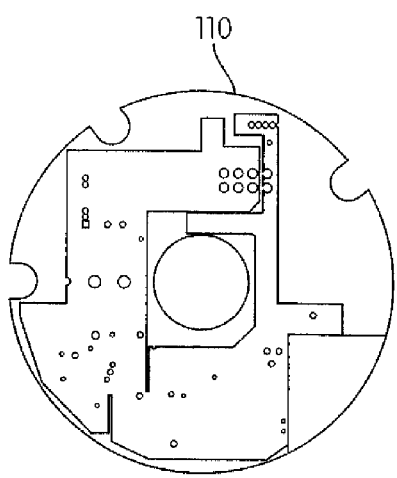
FIG. 8 shows a plan view of the power plane of the printed circuit board assembly.

FIGS. 4 and 5 disclose the upper surface 104 and the lower surface 106 of printed circuit board assembly 100. FIG. 5 depicts the traces that are characteristic of a printed circuit board assembly.

PCB assembly 100 includes a microcontroller 120 which preferably may include non-volatile memory, e.g., electrically-erasable programmable read-only memory integrated circuit (EEPROM) or an alternative type of non-volatile rewriteable memory such as flash memory, a linear single cell lithium ion charger 134, an impedance track battery fuel gauge 136, a low noise regulator (not shown), an RS 232 transceiver 138, a radio frequency (RF) transceiver which may or may not be integrated into microcontroller 120 (not shown), accelerometer 140, and an antenna 150, which are in electronic communication through printed circuit traces on the substrate 170. Non volatile memory portion of microcontroller 120 may in various alternate embodiments be something other than EEPROM, e.g., flash memory, other forms of read-only memory that is capable of retaining stored information when power is lost. In at least one exemplary embodiment RF transceiver may be a 2.4 GHz RE transceiver, and the antenna configured for 2.45 GHz antenna transmission. Other receiver and antenna configurations may be used, provided that the transceiver and antenna are matched. In the exemplary embodiment the transceiver operates over a range of from about 2405 MHz to about 2480 MHz, and the antenna operates over about substantially the same range. The transceiver selects a channel in the range. Broadly stated, RF transceiver and antenna may be configured for any RF frequency provided that they are compatibly tuned to the selected frequency. The voltage regulator may be preferably configured for 2.5 volts, although a voltage regulator for any suitable operating voltage may be used. Also included on PCB assembly 100 may be a wake-up switch 160, potentiometer 132, and miscellaneous circuit elements—resistors, capacitors, inductors, external connectors, test points, and voltage suppressors.

Microcontroller 120 provides logic control for all of the components and wireless communications between foot pedal 10 and remotely-controlled devices. For example, communications and logic control may include software, hardware and combinations thereof for synchronizing foot pedal 10 with one or more wireless dental handpiece or other dental or medical instruments for selectively pairing and controlling the instrument. In at least one exemplary embodiment battery capacity measuring device 136 may be a System-Side Impedance Track Fuel Gauge, model no. BQ27500DRZT manufactured by Texas Instruments of Dallas, Tex., or a microcontroller having comparable operating characteristics. Any microcontroller known in the art is suitable for use herein regardless of amount of flash memory and RAM.

Antenna 150 is connected through a balun (not shown) to the transceiver 139 to provide RF input signals to transceiver 139. Antenna 150 is configured for communications in the appropriate standard, e.g., ZigBee, Bluetooth, IEEE 802.11 or telemetry.

Transceiver 139 may be, for example in a preferred embodiment, a ZigBee™ compliant platform 2.4 GHz low power transceiver plus microcontroller or other transceiver capable of compliance with IEEE® 802.15.4 standard. Transceiver 139 may be an RE transceiver which is an 802.15.4 standard compliant radio that operates in the 2.4 GHz ISM frequency band. Transceiver 139 may include a low noise amplifier, 1 mW nominal output power, with internal voltage controlled oscillator (VCO), integrated transmit/receive switch, on-board power supply regulation, and full spread-spectrum encoding and decoding. Transceiver 139 may preferably include a microcontroller unit, for example, an 8 bit S08-based microcontroller unit by FreeScale Semiconductor. Inc., of Austin, Tex. In the exemplary embodiment shown in FIG. 4, transceiver 139 is incorporated into microprocessor, or microcontroller unit 120, however in alternate embodiments the transceiver can be separated from microprocessor 120. Transceiver 139 is preferably located between microprocessor 120 and antenna 150.

RS232 transceiver 138 provides an electrical interface between an asynchronous communication controller and the serial-port connector for handling data communications, although in an alternate embodiment transceiver 138 may include a different type of serial interface, e.g., USB and comparable serial interfaces.

An accelerometer 140 detects when foot pedal 10 is in a level and upright position to permit operation of foot pedal 10. If foot pedal 10 is tilted or not upright and level, i.e., in the intended position for use, controller inhibits any motor enabling transmission of signals between the handpiece and foot pedal 10 and keeps foot pedal 10 from operating the handpiece until it is returned to the proper orientation. In one embodiment accelerometer 140 is an integrated-circuit accelerometer. Accelerometer 140 may also detect vibration in foot pedal 10.

In an alternate embodiment, accelerometer 140 may include a capacitive sensing cell (g-cell) and a signal conditioning ASIC. The g-cell is a mechanical structure formed from semiconductor materials. The ASIC uses switched capacitor techniques to measure the g-cell capacitors and extract the acceleration data from the difference between the two capacitors. The ASIC also signal conditions and filters the signal, providing an output voltage that is ratiometric and proportional to acceleration. Ratiometric means that the output offset voltage and sensitivity is scaled substantially linearly with applied supply voltage. As supply voltage is increased, the sensitivity and offset increase linearly; as supply voltage decreases, offset and sensitivity decrease linearly. In an alternate embodiment, the accelerometer 140 may provide a sleep mode feature to conserve battery power during extended periods when foot pedal 10 is not in use. When sleep mode is active, accelerometer 140 outputs are turned off to reduce of operating current. When a wake-up signal is received by accelerometer 140, it resumes a normal mode of operation.

In another exemplary embodiment, accelerometer 140 may also include a self test feature to permit verification of the mechanical and electrical integrity of accelerometer 140. In another embodiment, accelerometer 140 may include plural sensitivity settings—referred to as g-select settings—which allows for the selection between two or more sensitivities. Depending on the a logic input signal, accelerometer 140 internal gain may be changed to allow it to function, for example, with a 3 g or 11 g sensitivity. The g-Select option can be omitted if foot pedal 10 requires only a single, e.g., 3 g, sensitivity.

A wake-up switch 160 may be used to detect vertical depression of cover 20 on foot pedal 10, and generate a wake-up signal to the system. In an alternate embodiment, wake-up switch 160 may also detect tilt and vibration. The signal level may be read directly by a digital input and used to interrupt or wake up microcontroller/EEPROM 120, or counted to estimate the amount and duration of activity. If foot pedal 10 is not in an upright operating position, for example if inadvertently kicked by the operator, foot pedal 10 may be disabled to prevent accidental initiation of control signals to one of the associated dental instruments. While a wake-up switch is used in the exemplary embodiment, other methods to awaken the system may be used, such as an RF source or accelerometer, or any external energy source with an energy sensing transducer.

Referring next to FIGS. 5-8, substrate 170 includes a composite of four layers, a top layer 104 on which components are mounted, a power plane 110 for power connections, a ground plane 114 for grounding connections, and a bottom layer 106 for soldering components to substrate 170. Exemplary layers 106, 104, 110, 114, are illustrated in FIGS. 5-9. Substrate 170 supports components mounted on top layer 104 and provides electrical interconnections and external connection points for the components. Substrate 170 is generally planar, disk-shaped, with a circular profile that conforms generally to the shape of foot pedal 10 housing and aperture 112 to allow plunger housing assembly 700 to pass through substrate 170.

While only certain features and embodiments of the invention have been shown and described, many modifications and changes may occur to those skilled in the art (for example, variations in sizes, dimensions, structures, shapes and proportions of the various elements, values of parameters (for example, temperatures, pressures, etc.), mounting arrangements, use of materials, colors, orientations, etc.) without materially departing from the novel teachings and advantages of the subject matter recited in the claims. The order or sequence of any process or method steps may be varied or re-sequenced according to alternative embodiments. It is, therefore, to be understood that the appended claims are intended to cover all such modifications and changes as fall within the true spirit of the invention. Furthermore, in an effort to provide a concise description of the exemplary embodiments, all features of an actual implementation may not have been described (i.e., those unrelated to the presently contemplated best mode of carrying out the invention, or those unrelated to enabling the claimed invention). It should be appreciated that in the development of any such actual implementation, as in any engineering or design project, numerous implementation specific decisions may be made. Such a development effort might be complex and time consuming, but would nevertheless be a routine undertaking of design, fabrication, and manufacture for those of ordinary skill having the benefit of this disclosure, without undue experimentation.

What is claimed is:

1. A printed circuit board for a wireless foot pedal control system comprising:
   a substrate for mounting a plurality of electronic components, the electronic components comprising:
      a programmable controller comprising a memory for storing software and data;
      a radio frequency transceiver configured for wireless communications with at least one remote wireless device;
      an accelerometer for generating an electronic wake-up signal to the programmable controller; and
      an antenna mounted on the substrate, the antenna communicatively coupled with the RF transceiver;
   the electronic components in electronic communication through printed circuit traces on the substrate, to control wireless communications between the foot pedal and the at least one other remote wireless device; and
   wherein the accelerometer detects if the foot pedal is tilted or upside down and transmits a position signal to the programmable controller and further detects vibration of the foot pedal and transmits a vibration signal;
   the programmable controller configured to:
      permit operation of the foot pedal when the position signal indicates that the foot pedal is in a predetermined position; and
      inhibit transmission of signals by the foot pedal when the position signal indicates that the foot pedal is not in the predetermined position; and
   wherein the accelerometer provides a sleep mode such that operating currents are reduced, and upon receipt of a wake-up signal indicative of the transmitted vibration signal from the accelerometer, the programmable controller resumes normal modes of operation.

2. The printed circuit board of claim 1, wherein the predetermined position of the foot pedal is a substantially level and upright position.

3. The printed circuit board of claim 1, wherein the accelerometer comprises an integrated-circuit accelerometer.

4. The printed circuit board of claim 1, wherein the accelerometer comprises a capacitive sensing cell and a signal conditioning application-specific integrated circuit that:
   measures the capacitive sensing cell and extracts acceleration data from a difference between two capacitors; and outputs a voltage signal that is proportional to acceleration and scaled substantially linearly with an applied supply voltage.

5. The printed circuit board of claim 1, wherein the accelerometer further comprises a self-test feature for verifying a mechanical and an electrical integrity of the accelerometer.

6. The printed circuit board of claim 1, wherein the accelerometer further comprises a plurality of sensitivity settings for the selection between two or more sensitivity levels.

7. The printed circuit board of claim 1, wherein the accelerometer detects a motion of the foot pedal and generates the wake-up signal that is transmitted to the programmable controller in response to detecting the motion.

8. The printed circuit board of claim 1, wherein the accelerometer detects a tilt and a vibration of the foot pedal, and disables the foot pedal in response to detecting the foot pedal not being in an upright operating position.

9. The printed circuit board of claim 1, wherein the accelerometer includes an external energy source with an energy sensing transducer.

10. The printed circuit board of claim 1, wherein the substrate comprises a top layer, a bottom layer, a power plane and a ground plane, wherein:
    the top layer comprises components mounted thereon, the power plane comprise power connections, the ground plane comprises grounding connections, and the bottom layer comprises solder connections of the electronic components to the substrate.

11. The printed circuit board of claim 10, wherein the substrate comprises a generally planar, disk-shaped member that conforms generally with a shape of the foot pedal housing, the printed circuit board further comprising an aperture configured to receive plunger housing assembly therethrough.

12. The printed circuit board of claim 1, wherein the radio frequency transceiver is configured as a 2.4 GHz RF transceiver, and the antenna is configured for an antenna transmission frequency of 2.45 GHz.

13. The printed circuit board of claim 1, wherein the transceiver is a broad band transceiver, and the transceiver is configured to operate over a frequency range of about 2405-2480 MHz; and wherein the antenna is configured for the same frequency range as the transceiver.

14. A wireless foot pedal controller for communication with at least one wireless dental instrument, comprising:
    a housing;
    a power source and a printed circuit board positioned within the housing, the printed circuit board connected to receive power from the power source;
    an analog to digital signal converter; and
    the printed circuit board comprising a substrate for mounting a plurality of electronic components, the electronic components comprising:
       a programmable controller comprising non-volatile memory for storing software and data;
       a radio frequency transceiver for wireless communications with at least one other remote wireless device;
       an accelerometer for generating an electronic wake-up signal to the controller, and to detect tilt and vibrations of the foot pedal; and
    an antenna mounted on the printed circuit board;
    the electronic components in electronic communication through printed circuit traces on the substrate, to control wireless communications between the foot pedal and the at least one other remote wireless device;

wherein the accelerometer detects if the foot pedal is tilted or upside down and transmits a position signal to the programmable controller;

the programmable controller configured to:
  permit operation of foot pedal when the position signal indicates that the foot pedal is in a predetermined position; and
  inhibit transmission of signals between the handpiece and foot pedal when the position signal indicates that the foot pedal is not in the predetermined position; and
  wherein the accelerometer provides a sleep mode such that operating currents are reduced, and upon receipt of the wake-up signal, corresponding to the detected vibrations of the foot pedal, from the accelerometer, the programmable controller resumes normal modes of operation.

15. The wireless foot pedal controller of claim 14, wherein the wake-up device detects a motion of the foot pedal controller and generates the wake-up signal to the programmable controller in response to detecting the motion.

* * * * *